United States Patent
Feng et al.

(10) Patent No.: US 10,729,639 B2
(45) Date of Patent: Aug. 4, 2020

(54) FAST DRYING NAIL POLISH TOPCOAT

(71) Applicant: L'ORÉAL, Paris (FR)

(72) Inventors: Jianxin Feng, Clark, NJ (US);
Ramakrishnan Hariharan, Springfield, NJ (US)

(73) Assignee: L'ORÉAL, Paris (FR)

( * ) Notice: Subject to any disclaimer, the term of this patent is extended or adjusted under 35 U.S.C. 154(b) by 0 days.

(21) Appl. No.: 16/050,222

(22) Filed: Jul. 31, 2018

(65) Prior Publication Data

US 2020/0038307 A1 Feb. 6, 2020

(51) Int. Cl.
| | | |
|---|---|---|
| *A61K 8/73* | (2006.01) | |
| *A61Q 3/02* | (2006.01) | |
| *A61K 8/31* | (2006.01) | |
| *A61K 8/84* | (2006.01) | |

(52) U.S. Cl.
CPC .............. *A61K 8/731* (2013.01); *A61K 8/31* (2013.01); *A61K 8/84* (2013.01); *A61Q 3/02* (2013.01)

(58) Field of Classification Search
CPC .. A61Q 3/02; A61K 2800/43; A61K 2800/95; A61K 8/466; A61K 8/731; A61K 8/87
See application file for complete search history.

(56) References Cited

U.S. PATENT DOCUMENTS

| | | |
|---|---|---|
| 4,798,720 A | 1/1989 | Holder |
| 5,130,125 A | 7/1992 | Martin et al. |
| 5,275,807 A | 1/1994 | Pappas et al. |
| 5,512,273 A | 4/1996 | Martin |
| 5,639,447 A | 6/1997 | Patel |
| 5,747,019 A | 5/1998 | Weisman |
| 5,785,958 A | 7/1998 | Sirdesai et al. |
| 6,051,242 A | 4/2000 | Patel et al. |
| 7,101,958 B2 | 9/2006 | Gloeckner et al. |
| 7,183,372 B2 | 2/2007 | Andrejewski et al. |
| 9,603,786 B1 | 3/2017 | Crescimanno |
| 2009/0012245 A1 | 1/2009 | Glockner et al. |
| 2017/0119656 A1* | 5/2017 | Xu .................. A61K 8/895 |

FOREIGN PATENT DOCUMENTS

JP 2015182976 A 10/2015

* cited by examiner

*Primary Examiner* — Nannette Holloman
(74) *Attorney, Agent, or Firm* — Meagher Emanuel Laks Goldberg & Liao, LLP.

(57) ABSTRACT

The invention presents a fast-drying nail polish topcoat composition with high shine and long wear. The disclosed combination of at least two cellulose-derived primary film formers, a ketone-aldehyde resin, a plasticizer, a hydrocarbon oil, and solvents selected such that no more than 20% of the solvents have an evaporation rate less than or equal to butyl acetate provides a nail polish that can be dried within 30 seconds on fingernails without sacrificing other critical properties.

19 Claims, No Drawings

FAST DRYING NAIL POLISH TOPCOAT

FIELD OF THE INVENTION

The present invention relates to nail polish topcoat compositions, and specifically to fast-drying nail polish topcoat compositions comprising cellulose-based film formers, a ketone-aldehyde resin, and particular selections of solvents.

BACKGROUND

Consumers use nail polish to cosmetically enhance the appearance of their nails or protect the nails from the abuses found in their everyday environment. Often this requires a nail polish that is formulated to provide a good shine.

Consumers also desire a durable nail polish. Lack of durability is often evidenced by unsightly chipping or peeling of the coating soon after the original coating has been applied, requiring at least in part a reapplication of the coating in an attempt to recreate the aesthetic appearance or the therapeutic benefits of the original nail coating. Application and/or removal of more durable nail coatings is often very time consuming, requiring long cure times upon administration by skilled personnel leading to added costs for the consumer.

Modern, fast-paced consumers desire a nail polish topcoat with an easy application that dries rapidly. Fast-dry nail polish topcoat is generally achieved through the selection of volatile solvent system selection and introduction of specific film formers which can gives topcoat desirable properties such as fast-solvent releasing, high clarity, high gloss, durability, good adhesion and stability.

Selection of solvent package is critical to shorten the drying time of topcoat. Volatile solvents with high evaporation rate can be chosen for this purpose. However, the fast evaporation of solvents in nail polishes when applied to manicure or pedicure could lead to undesired properties such as streaking, air bubbling, hazing, and reduced gloss and adhesion. Further, some of solvents that evaporate quickly—toluene and acetone, for example—are toxic.

A number of efforts have been made to take advantage of appropriate solvent combination to achieve fast drying speed as well as high shine and long wear. Thus, a fast-drying nail polish topcoat that retains shine and long wear, is therefore highly desirable.

BRIEF SUMMARY

The present invention is directed to a nail polish topcoat composition that is toluene and acetone-free, having (a) at least two cellulose-derived primary film formers; (b) a ketone-aldehyde resin; (c) at least one plasticizer; (d) a hydrocarbon oil; and (e) a solvent having an evaporation rate greater than butyl acetate, wherein the nail polish topcoat composition comprises less than about 20% of solvents having an evaporation rate less than or equal to butyl acetate.

Advantageously, the primary film formers may be present in a total amount ranging from about 11% to about 17% by weight, and a first film former may be present in an amount less than about 5% by weight. Also advantageously, ranging from about 1% to about 2% by weight. Also advantageously, the primary film formers may consist of nitrocellulose and cellulose acetate butyrate.

It may also be advantageous for the ketone-aldehyde resin is a hydrogenated acetophenone/oxymethylene copolymer, or be present in an amount from about 1% to about 7% by weight.

It may also be advantageous for the hydrocarbon oil to include a branched hydrocarbon having between 6 and 68 carbons, to specifically include $C_9$-$C_{12}$ alkanes or $C_6$-$C_9$ alcohols, and/or to be present in an amount from about 0.5% to about 2% by weight.

It may also be advantageous for the nail polish topcoat to include a non-polar silicone copolymer, such as an acrylate/dimethicone copolymer, and it may be further advantageous for the copolymer to be present in an amount less than about 0.5% by weight.

It is also advantageous when the solvent system is selected such that the one of the solvents has an evaporation rate at least four times that of butyl acetate, such as ethyl acetate.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "include", "includes" and "including" are meant to be non-limiting.

The present invention is directed to a nail composition having (a) at least two cellulose-derived primary film formers; (b) a ketone-aldehyde resin; (c) at least one plasticizer; (d) a hydrocarbon oil; and (e) a solvent having an evaporation rate greater than butyl acetate, where the nail polish composition is designed to utilize less than about 20% of solvents having an evaporation rate less than or equal to butyl acetate. Each of these will be discussed in turn.

According to embodiments of the present invention, the nail polish topcoat composition includes at least two cellulose-derived primary film formers. Suitable film formers may include, but are not limited to, nitrocellulose, cellulose propionate, cellulose acetate butyrate, and hydroxyethylcellulose, hydroxypropylcellulose, methylcellulose, and ethylhydroxyethylcellulose.

In some embodiments, the two film formers may have the same chemical name, but have different properties (e.g., two different grades of nitrocellulose). In some embodiments, the at least two cellulose-derived film formers include nitrocellulose and cellulose acetate butyrate. In some embodiments, the topcoat composition only has two cellulose-derived film formers.

A suitable cellulose-derived film former may include, but is not limited to, those sold by EASTMAN™ Chemical, including but not limited to EASTMAN™ Cellulose Acetate Butyrate.

In certain embodiments, the at least two cellulose-derived primary film formers are present in a total amount ranging from about 5% to about 25% by weight. Preferably, the at least two cellulose-derived primary film formers are present in a total amount ranging from about 8% to about 20% by weight. Still more preferably, the at least two cellulose-derived primary film formers are present in a total amount ranging from about 11% to about 17% by weight.

In certain embodiments, one of the cellulose-derived film formers is present in an amount less than about 5% by weight, preferably from about 1% to about 4% by weight, and still more preferably from about 1% to about 2% by weight. In certain embodiments, a second cellulose-derived film former is present in an amount ranging from about 5% to about 20% by weight, preferably from about 7% to about 18% by weight, and more preferably from about 10% to about 15% by weight.

In certain embodiments, the ratio of a first cellulose-derived film former to a second cellulose-derived film former is between 1:3 and 1:20, preferably between 1:5 and 1:18, and more preferably from about 1:8 to about 1:15.

According to embodiments of the present invention, the nail polish topcoat composition also includes a ketone-aldehyde resin.

In certain embodiments, the ketone-aldehyde resin is a copolymer comprising an aromatic ketone.

Potential ketone-aldehyde resins may include, but are not limited to, those described in U.S. Pub. No. 2009/0012245, U.S. Pat. Nos. 7,183,372 and 7,101,958, or those sold by Evonik Industries under the TEGO® Variplus brand, such as TEGO® Variplus SK.

In certain embodiments, the ketone-aldehyde resin is present in an amount less than about 10% by weight. Preferably, the resin is present in an amount from about 1% to about 7% by weight, and more preferably, from about 1% to about 5% by weight.

According to embodiments of the present invention, the nail polish topcoat composition also includes at least one plasticizer.

In certain embodiments, the plasticizer may include a benzoic acid derivative may be a dibenzoate ester, including but not limited to diethylene glycol dibenzoate, dipropylene glycol dibenzoate, and 1,2-propylene glycol dibenzoate. In certain embodiments, the plasticizer may include a citric acid derivative, and may be an optionally hydroxylated triester of a $C_2$-$C_8$ tricarboxylic acid and of a $C_2$-$C_8$ alcohol, such as citric acid esters, such as trioctyl citrate, triethyl citrate, acetyl tributyl citrate, or tributyl citrate. Plasticizers may include acetyl tributyl citrate, such as those sold under Citroflex brand by Vertellus, or the Uniplex brand by Unitex Chemical. In certain embodiments, the plasticizer may be a $C_1$-$C_6$ carboxylic acid ester of sucrose such as sucrose acetate isobutyrate. In certain embodiments, the at least one plasticizer may be a combination of plasticizers, such as a combination of one or more of dipropylene glycol dibenzoate, acetyl tributyl citrate, and/or sucrose acetate isobutyrate.

The one or more plasticizers may be present in an amount ranging from about 1% to about 20% by weight, more preferably from about 1% to about 10% by weight, and still more preferably from about 1% to about 5% by weight.

According to embodiments of the present invention, the nail polish topcoat composition also includes a hydrocarbon oil.

"Hydrocarbon oil" refers to a compound which is liquid at room temperature, is insoluble in water and is of hydrophobic character. The hydrocarbon oils used in conformity with the invention are typically synthetic oils, mineral, vegetable or animal oils, unsaturated fatty alcohols, and esters of fatty acids and lower $C_2$-$C_4$ mono- or polyalcohols.

In preferred embodiments, the hydrocarbon oils are acyclic.

In some embodiments, the hydrocarbon oils include but are not limited to substituted or unsubstituted hydrocarbon chains having between 6 and 68 carbons, and more preferably between 6 and 24 carbons. Preferred substituents may include hydroxyl groups. In some preferred embodiments, the hydrocarbon oils may be $C_9$-$C_{12}$ alkanes or $C_6$-$C_9$ alcohols.

In some embodiments, the hydrocarbon oils are branched hydrocarbon chains having between 6 and 68 carbons, which may include, but are not limited to such hydrocarbons as isododecane, isohexadecane, isoeicosane, and polyisobutene, including those sold under the PERMETHYL® brand by Presperse Inc. Preferred embodiments have chains having between 12 and 24 carbons. These may be used alone or in combination with other isoparaffins having higher molecular weights, such as highly branched hydrocarbon chains having between 76 and 144 carbons, such as PERMETHYL® 106A from Presperse Inc. The hydrocarbon oil may also include $C_6$-$C_{12}$ fatty acid triglycerides or liquid paraffin. Alternatively, the hydrocarbon oil may include animal oils chosen from naturally or chemically saturated oils such as squalene, or vegetable oils such as almond, avocado, coconut, or olive oils. Naturally or chemically saturated oils are preferred.

The one or more hydrocarbon oils may be present in an amount ranging from about 1% to about 20% by weight, more preferably from about 1% to about 10% by weight, and still more preferably from about 0.5% to about 5% by weight.

According to embodiments of the present invention, the nail polish topcoat composition also includes a solvent having an evaporation rate greater than butyl acetate.

According to embodiments of the present invention, the nail composition also includes at least one solvent having an evaporation rate greater than butyl acetate. In certain embodiments, the solvent comprises at least one acetic acid ester having a $C_1$-$C_4$ alkyl group, including but not limited to, methyl acetate, ethyl acetate, n-propyl acetate, and isopropyl acetate. For example, in some embodiments, the at least one solvent consists of ethyl acetate. In certain embodiments, the solvent comprises at least one alcohol having a $C_1$-$C_4$ alkyl group. For example, in some embodiments, the at least one solvent consists of ethyl acetate and at least one of either ethanol, propyl acetate and/or isopropanol.

In certain embodiments, the solvent comprises a combination of at least one solvent having an evaporation rate greater than butyl acetate and at least one solvent having evaporation rate less than or equal to butyl acetate. For example, in some embodiments, the at least one solvent consists of ethyl acetate, propyl acetate, isopropanol, and butyl acetate.

In certain embodiments, the ratio of the evaporation rate of the solvent to that of butyl acetate is greater than 2, more preferably greater than 3, and more preferably greater than 4. In certain embodiments, the ratio is between 2 and 8, more preferably between 3 and 7, and still more preferably between 4 and 6.

Although the present invention may utilize solvents having an evaporation rate less than or equal to butyl acetate, the nail polish composition should be designed such that less than about 20% of the solvents have an evaporation rate less than or equal to butyl acetate.

The solvent having an evaporation rate greater than butyl acetate may be present in an amount ranging from about 10% to about 90% by weight. In preferred embodiments, the at least one solvent may be present in an amount ranging from about 30% to about 85% by weight, and more preferably from about 50% to about 80% by weight.

In certain embodiments, the content of all evaporative solvents, including, e.g., butyl acetate, are present in an amount between about 60% and about 90% by weight.

According to embodiments of the present invention, the nail polish topcoat composition may also include a non-polar silicone copolymer. In certain embodiments, the non-polar silicone copolymer may comprise repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-543 or KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

The non-polar silicone copolymer may present in an amount ranging from about 0.01% to about 2% by weight. Preferably, the non-polar silicone copolymer may present in an amount ranging from about 0.01% to about 1% by weight, more preferably from about 0.05% to about 0.6% by weight.

In certain embodiments, the nail polish topcoat composition may also include other compounds known to those in the art, which may include also include a colorant (coloring agent). The at least one colorant, if present, will typically be present in an amount less than 1% by weight, more typically less than 0.5%, and still more typically less than 0.1%. The other compounds may also include a drying agent, such as PDMS.

In certain embodiments, polyols and/or polyol derivatives are also included. The term "polyol" is used to refer to organic molecules comprising at least two hydroxyl (OH) functions.

The term "polyol" thus includes in particular sugars, and also derivatives thereof. For the purposes of the invention, the term "polyol" is intended to mean in particular: a branched or unbranched, saturated or unsaturated, linear hydrocarbon-based chain comprising at least two hydroxyl functions; or a branched or unbranched, saturated linear hydrocarbon-based chain in which one or more carbon atoms are replaced with an oxygen atom and which comprises at least two hydroxyl functions, for instance polyethylene glycols (PEGs) having from 4 to 8 ethylene glycol units.

Preferably, the polyol of the composition according to the invention has a branched or unbranched, saturated linear hydrocarbon-based chain. Advantageously, the polyol comprises a number of carbon atoms ranging from 2 to 20, and preferably from 2 to 10, and comprises from 2 to 12, and better still from 2 to 8, hydroxyl functions. The polyols of the composition according to the invention can be chosen from ethylene glycol, propylene glycol, 1,3-propanediol, isoprene glycol, butylene glycol, dipropylene glycol, polypropylene glycol, glycerol, glycerine, diglycerine, erythritol, pentaerythrytol, arabitol, adonitol, sorbitol, dulcitol, maltitol, panthenol, preferably glycerine, propylene glycol, dipropylene glycol, butylene glycol and 1,3-propanediol, and mixtures thereof. In particular, the polyol is chosen from propylene glycol, dipropylene glycol and glycerine. Preferably, the polyol is glycerine. The polyol derivatives include in particular polyol esters and ethers.

The polyol(s) and derivatives may be present in an amount from about 0.1% to about 10% by weight, and more preferably from about 1% to about 7% by weight.

Examples

Variations of the general composition listed in Table 1 were prepared by mixing in all the components at room temperature, one at a time, except the colorant and the non-polar silicone polymer. Then the colorant was added and mixed until homogenous, and finally the non-polar silicone polymer was added and mixed until homogenous.

TABLE 1

| Material | Ex. 1 |
| --- | --- |
| Base film formers | 15-30% |
| Plasticizers | 1-7% |
| Drying Agent | <1% |
| Hydrocarbon Oils | <5% |
| Plasticizer | 1-7% |
| Solvents | 60-90% |
| Colorants | <0.5% |
| Ketone-Aldehyde Resin | 1-7% |

Evaluative testing results are shown in Table 2, showing the results from four batches, where the only variable was the amount of ketone-aldehyde resin, adjusting the solvent system to q.s. to 100%. Comparative examples without, e.g., the claimed ketone-aldehyde resin also dry rapidly, but do have significantly poorer performance characteristics such as, e.g., shine.

TABLE 2

| % Ketone-Aldehyde Resin | Shine at 20° (1 day) | Shine at 60° (1 day) | Touch Time To Dry (seconds) |
| --- | --- | --- | --- |
| 1% | 78.2 ± 0.2 | 85.7 ± 0.2 | 20 |
| 2% | 79.0 ± 0.2 | 86.7 ± 0.1 | 25 |
| 4% | 81.7 ± 0.6 | 88.8 ± 0.1 | 25 |
| 6% | 83.7 ± 0.5 | 90.6 ± 0.1 | 25 |

Those skilled in the art will recognize, or be able to ascertain using no more than routine experimentation, many equivalents to the specific embodiments of the invention described herein. Such equivalents are intended to be encompassed by the following claims.

What is claimed:

1. A nail polish topcoat that is toluene and acetone-free, comprising:
    at least two cellulose-derived primary film formers including a first cellulose-derived primary film former;
    a ketone-aldehyde resin;
    at least one plasticizer;
    a hydrocarbon oil; and
    at least one solvent, wherein the nail polish topcoat comprises less than about 20% by weight of solvents having an evaporation rate less than or equal to butyl acetate and greater than about 80% by weight of solvents having an evaporation rate greater than butyl acetate.

2. The nail polish topcoat according to claim 1, wherein the at least two cellulose-derived primary film formers are present in a total amount ranging from about 11% to about 17% by weight.

3. The nail polish topcoat according to claim 1, wherein the at least two cellulose-derived primary film formers consist of cellulose acetate butyrate and nitrocellulose.

4. The nail polish topcoat according to claim 1, wherein the first cellulose-derived primary film former is present in an amount less than about 5% by weight.

5. The nail polish topcoat according to claim 1, wherein the ketone-aldehyde resin is a hydrogenated acetophenone/oxymethylene copolymer.

6. The nail polish topcoat according to claim 1, wherein the ketone-aldehyde resin is present in an amount ranging from about 1% to about 7% by weight.

7. The nail polish topcoat according to claim 1, wherein the hydrocarbon oil comprises a substituted or unsubstituted hydrocarbon having between 6 and 68 carbons.

8. The nail polish topcoat according to claim 7, wherein the hydrocarbon oil comprises $C_9$-$C_{12}$ alkanes or $C_6$-$C_9$ alcohols.

9. The nail polish topcoat according to claim 1, wherein the hydrocarbon oil is present in an amount ranging from about 0.5% to about 2% by weight.

10. The nail polish topcoat according to claim 1, further comprising a non-polar silicone copolymer.

11. The nail polish topcoat according to claim 10, wherein the non-polar silicone copolymer is an acrylate/dimethicone copolymer.

12. The nail polish topcoat according to claim 10, wherein the non-polar silicone copolymer is present in an amount less than or equal to 0.5% by weight.

13. The nail polish topcoat according to claim 1, wherein the solvent having an evaporation greater than butyl acetate has an evaporation rate at least four times that of butyl acetate.

14. The nail polish topcoat according to claim 1, wherein the at least one solvent having an evaporation rate greater than butyl acetate is ethyl acetate.

15. The nail polish topcoat according to claim 1, wherein the nail polish topcoat comprises at least four solvents.

16. The nail polish topcoat according to claim 1, wherein the at least one plasticizer is present in an amount ranging from 1% to 5%.

17. The nail polish topcoat according to claim 1, wherein the nail polish topcoat comprises at least two plasticizers selected from the group consisting of a dibenzoate ester, a citric acid derivative, and a $C_1$-$C_6$ carboxylic acid ester of sucrose.

18. The nail polish topcoat according to claim 17, wherein the nail polish topcoat comprises a dibenzoate ester, a citric acid derivative, and a $C_1$-$C_6$ carboxylic acid ester of sucrose.

19. The nail polish topcoat according to claim 1, wherein the at least two cellulose-derived primary film formers are different grades of nitrocellulose.

* * * * *